US012788990B2

(12) United States Patent
Bokil et al.

(10) Patent No.: US 12,788,990 B2
(45) Date of Patent: Nov. 10, 2026

(54) METHOD AND APPARATUS FOR PROGRAMMING PATTERNED DEEP BRAIN STIMULATION

(71) Applicant: Boston Scientific Neuromodulation Corporation, Valencia, CA (US)

(72) Inventors: Hemant Bokil, Cambridge, MA (US); G. Karl Steinke, Valencia, CA (US); Archie Eslabon Huerto, Simi Valley, CA (US); Dennis Allen Vansickle, Lancaster, CA (US); Sridhar Kothandaraman, Valencia, CA (US); John Rivera, Oxnard, CA (US); Mary Kotchevar, Minneapolis, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 269 days.

(21) Appl. No.: 18/503,811

(22) Filed: Nov. 7, 2023

(65) Prior Publication Data

US 2024/0149066 A1 May 9, 2024

Related U.S. Application Data

(60) Provisional application No. 63/423,361, filed on Nov. 7, 2022.

(51) Int. Cl.

| | |
|---|---|
| ***A61N 1/36*** | (2006.01) |
| ***A61N 1/372*** | (2006.01) |
| ***G16H 40/63*** | (2018.01) |

(52) U.S. Cl.

CPC ..... *A61N 1/36146* (2013.01); *A61N 1/37247* (2013.01); *G16H 40/63* (2018.01)

(58) Field of Classification Search

CPC ............ A61N 1/36146; A61N 1/37247; A61N 1/0534; A61N 1/36025; A61N 1/36082;

(Continued)

(56) References Cited

U.S. PATENT DOCUMENTS 11,305,123 B2 4/2022 Steinke
2010/0292754 A1* 11/2010 Gliner ................ A61N 1/36178 607/45

(Continued)

FOREIGN PATENT DOCUMENTS

WO WO-2024102721 A1 5/2024

OTHER PUBLICATIONS

"International Application Serial No. PCT/US2023/078933, International Preliminary Report on Patentability mailed May 15, 2025", 8 pgs.

(Continued)

*Primary Examiner* — Eugene T Wu
(74) *Attorney, Agent, or Firm* — Schwegman Lundberg & Woessner, P.A.

(57) ABSTRACT

An example of a system for delivering neurostimulation from a stimulation device may include a programming control circuit and a programming control circuit. The programming control circuit may be configured to generate information for programming the stimulation device to deliver the neurostimulation according to a pattern of neurostimulation pulses. The stimulation programming circuit may be configured to: receive goal option(s) selected from a plurality of goal options each including at least one goal for deep brain stimulation; select programmability option(s) associated with the received goal option(s) from a plurality of programmability options each allowing one or more aspects of the pattern of neurostimulation pulses and/or its delivery to be programmable; receive programming information required by the selected programmability option(s); and determine the pattern of neurostimulation pulses for the selected goal option(s) using the received programming information.

20 Claims, 8 Drawing Sheets

(58) Field of Classification Search
CPC ............ A61N 1/37514; A61N 1/36175; A61N 1/36178; G16H 40/63; G16H 20/30
See application file for complete search history.

(56) References Cited

U.S. PATENT DOCUMENTS

| | | | | |
|---|---|---|---|---|
| 2016/0375258 | A1* | 12/2016 | Steinke ................ | A61N 1/0551 607/59 |
| 2017/0056642 | A1 | 3/2017 | Moffitt et al. | |
| 2017/0106197 | A1 | 4/2017 | Wechter et al. | |
| 2018/0214699 | A1 | 8/2018 | Kothandaraman et al. | |
| 2019/0054306 | A1 | 2/2019 | Steinke et al. | |
| 2019/0168002 | A1 | 6/2019 | Steinke et al. | |

OTHER PUBLICATIONS

"International Application Serial No. PCT/US2023/078933, International Search Report mailed Feb. 29, 2024", 5 pgs.
"International Application Serial No. PCT/US2023/078933, Written Opinion mailed Feb. 29, 2024", 6 pgs.

* cited by examiner

METHOD AND APPARATUS FOR PROGRAMMING PATTERNED DEEP BRAIN STIMULATION

CLAIM OF PRIORITY

This application claims the benefit of U.S. Provisional Application No. 63/423,361, filed on Nov. 7, 2022, which is hereby incorporated by reference in its entirety.

TECHNICAL FIELD

This document relates generally to neurostimulation and more particularly to a system for delivering deep brain stimulation to a patient using patterned (non-tonic) stimulation waveforms.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical pulses. The delivery is controlled using stimulation parameters that specify spatial (where to stimulate), temporal (when to stimulate), and informational (patterns of pulses directing the nervous system to respond as desired) aspects of the electrical pulses. Studies in neuroscience and neurostimulation have suggested a need for varying the stimulation parameters specifying one, two, or all three of these aspects for DBS therapies to improve therapeutic efficacy and expand applications to more indications. A neurostimulation system (e.g., including the implantable neurostimulator and the external programming device) needs to be capable of programming the stimulation parameters to accommodate such a need.

SUMMARY

An example (e.g., "Example 1") of a system for delivering neurostimulation from a stimulation device is provided. The system may include a programming control circuit and a programming control circuit. The programming control circuit may be configured to generate information for programming the stimulation device to deliver the neurostimulation according to a pattern of neurostimulation pulses. The stimulation programming circuit may be configured to: receive one or more goal options selected from a plurality of goal options each including at least one goal for deep brain stimulation (DBS); select one or more programmability options associated with the received one or more goal options from a plurality of programmability options each allowing one or more aspects of at least one of the pattern of neurostimulation pulses or the delivery of the neurostimulation according to the pattern of neurostimulation pulses to be programmable; receive programming information required by the selected one or more programmability options; and determine the pattern of neurostimulation pulses for the selected one or more goal options using the received programming information.

In Example 2, the subject matter of Example 1 may optionally be configured to further include a user interface including a presentation device, a user input device, and the stimulation programming circuit, and such that the stimulation programming circuit is configured to: present the plurality of goal options using the presentation device; receive a user selection of the one or more goal options from the plurality of goal options using the user input device; present the selected one or more programmability options using the presentation device; and receive at least a portion of the programming information required by the selected one or more programmability options using the user input device.

In Example 3, the subject matter of any one or any combination of Examples 1 and 2 may optionally be configured such that the stimulation programming circuit is configured to allow for: composition of a stimulation program using the received programming information, the stimulation program including stimulation parameters defining the pattern of neurostimulation pulses; and composition of program building blocks of the stimulation program, the program building blocks each including a subset of the stimulation parameters defining a segment of the pattern of neurostimulation pulses.

In Example 4, the subject matter of Example 3 may optionally be configured such that the stimulation programming circuit is configured to allow for composition of pulses, blocks, and sequences of the program building blocks. The pulses are each a pulse of the pattern of neurostimulation pulses. The blocks include stimulation blocks during which pulses of the pattern of neurostimulation pulses are to be delivered and non-stimulation blocks during which no pulse of the pattern of neurostimulation pulses is to be delivered. The sequence each include multiple blocks each being a stimulation block or a non-stimulation block.

In Example 5, the subject matter of any one or any combination of Examples 3 and 4 may optionally be configured such that the stimulation programming circuit is further configured to allow for scheduling of applications of the stimulation program for controlling the delivery of the pattern of neurostimulation pulses.

In Example 6, the subject matter of any one or any combination of Examples 2 to 5 may optionally be configured such that the stimulation programming circuit is configured to determine stimulation parameters associated with each programmability option of the selected one or more programmability options using the presentation device and the user input device.

In Example 7, the subject matter of Example 6 may optionally be configured such that the stimulation programming circuit is configured to determine the stimulation parameters associated with the each programmability option by presenting values or a value range for each stimulation parameter using the presentation device and receiving a value selected from the presented values or a value within the presented value range using the user input device.

In Example 8, the subject matter of any one or any combination of Examples 2 to 7 may optionally be configured such that the stimulation programming circuit is configured to: present the plurality of goal options including at least a goal option of multi-symptom control using the presentation device; and select the one or more programmability options including at least one of a programmability option of various stimulation frequency combinations or a programmability option of program scheduling in response to the goal option of multi-symptom control being selected.

In Example 9, the subject matter of any one or any combination of Examples 2 to 8 may optionally be configured such that the stimulation programming circuit is configured to: present the plurality of goal options including at least a goal option of power efficiency using the presentation device; and select the one or more programmability options including at least a programmability option of active recharge options in response to the goal option of multi-symptom control being selected.

In Example 10, the subject matter of any one or any combination of Examples 2 to 9 may optionally be configured such that the stimulation programming circuit is configured to: present the plurality of goal options including at least a goal option of prevention of habituation using the presentation device; and select the one or more programmability options including at least one of a programmability option of microburst and cycling, a programmability option of program scheduling, or a programmability option of pulse-by-pulse patterning in response to the goal option of prevention of habituation being selected.

In Example 11, the subject matter of any one or any combination of Examples 2 to 10 may optionally be configured such that the stimulation programming circuit is configured to: present the plurality of goal options including at least a goal option of providing desynchronizing therapy using the presentation device; and select the one or more programmability options including at least one of a programmability option of microburst and cycling or a programmability option of pulse-by-pulse patterning in response to the goal option of providing desynchronizing therapy being selected.

In Example 12, the subject matter of any one or any combination of Examples 2 to 11 may optionally be configured such that the stimulation programming circuit is configured to: present the plurality of goal options including at least a goal option of plasticity induction using the presentation device; and select the one or more programmability options including at least one of a programmability option of microburst and cycling or a programmability option of pulse-by-pulse patterning in response to the goal option of plasticity induction being selected.

In Example 13, the subject matter of any one or any combination of Examples 2 to 12 may optionally be configured such that the stimulation programming circuit is configured to: present the plurality of goal options including at least a goal option of precision targeting using the presentation device; and select the one or more programmability options including at least one of a programmability option of wide parameter range, a programmability option of microburst and cycling, or a programmability option of pulse-by-pulse patterning in response to the goal option of precision targeting being selected.

In Example 14, the subject matter of any one or any combination of Examples 1 to 7 may optionally be configured such that the plurality of goal options includes multi-symptom control, power efficiency, prevention of habituation, providing desynchronizing therapy, plasticity induction, and precision targeting.

In Example 15, the subject matter of Example 14 may optionally be configured such that the plurality of programmability options includes wide parameter range, various stimulation frequency combinations, active recharge options, microburst and cycling, program scheduling, and pulse-by-pulse patterning.

An example (e.g., "Example 16") of a method for delivering neurostimulation from a stimulation device is provided. The method may include: receiving by a processor one or more goal options selected from a plurality of goal options for deep brain stimulation (DBS); selecting using the processor one or more programmability options associated with the received one or more goal options from a plurality of programmability options each allowing one or more aspects of at least one of a pattern of neurostimulation pulses or the delivery of the neurostimulation according to the pattern of neurostimulation pulses to be programmable; receiving by the processor programming information required by the selected one or more programmability options; determining using the processor the pattern of neurostimulation pulses for the selected one or more goal options using the received programming information; and generating information using the processor for programming the stimulation device to deliver the neurostimulation according to the determined pattern of neurostimulation pulses.

In Example 17, the subject matter of receiving by the processor the one or more goal options as found in Example 16 may optionally include presenting the plurality of goal options using a user interface and receiving a user selection of the one or more goal options from the plurality of goal options using the user interface, and the subject matter of receiving by the processor programming information required by the selected one or more programmability options as found in Example 16 may optionally include presenting the selected one or more programmability options using the user interface and receiving user input related to at least a portion of the programming information required by the selected one or more programmability options using the user interface.

In Example 18, the subject matter of determining using the processor the pattern of neurostimulation pulses as found in any one or any combination of Examples 16 and 17 may optionally include composing at least one of a stimulation program or building blocks of the stimulation program using the received programming information The stimulation program includes stimulation parameters defining the pattern of neurostimulation pulses. The program building blocks each include a subset of the stimulation parameters defining a segment of the pattern of neurostimulation pulses.

In Example 19, the subject matter of composing the program building blocks as found in Example 18 may optionally include composing one or more of pulses, blocks, or sequences of the program building blocks. The pulses are each a pulse of the pattern of neurostimulation pulses. The blocks are each a stimulation block during which pulses of the pattern of neurostimulation pulses are to be delivered or a non-stimulation block during which no pulse of the pattern of neurostimulation pulses is to be delivered. The sequence each include multiple blocks of the blocks.

In Example 20, the subject matter of determining using the processor the pattern of neurostimulation pulses as found in any one or any combination of Examples 18 and 19 may optionally further include scheduling of applications of the stimulation program for controlling the delivery of the pattern of neurostimulation pulses.

In Example 21, the subject matter of determining using the processor the pattern of neurostimulation pulses as found in any one or any combination of Examples 17 to 20 may optionally further include determining stimulation parameters associated with each programmability option of the selected one or more programmability options using the user interface.

In Example 22, the subject matter of determining stimulation parameters associated with each programmability option of the selected one or more programmability options using the user interface as found in Example 21 may optionally include: presenting values or a value range for each stimulation parameter using the user interface; and receiving a value selected from the presented values or a value within the presented value range using the user interface.

In Example 23, the subject matter of presenting the plurality of goal options using the user interface as found in any one or any combination of Examples 17 to 22 may optionally include presenting the plurality of goal options including at least a goal option of multi-symptom control, and the subject matter of selecting using the processor one or more programmability options associated with the selected one or more goals as found in any one or any combination of Examples 17 to 22 may optionally include selecting the one or more programmability options including at least one of a programmability option of various stimulation frequency combinations or a programmability option of program scheduling in response to the goal option of multi-symptom control being selected.

In Example 24, the subject matter of presenting the plurality of goal options using the user interface as found in any one or any combination of Examples 17 to 23 may optionally include presenting the plurality of goal options including at least a goal option of power efficiency, and the subject matter of selecting using the processor one or more programmability options associated with the selected one or more goals as found in any one or any combination of Examples 17 to 23 may optionally include selecting the one or more programmability options including at least one of a programmability option of various stimulation frequency combinations or a programmability option of program scheduling in response to the goal option of multi-symptom control being selected.

In Example 25, the subject matter of presenting the plurality of goal options using the user interface as found in any one or any combination of Examples 17 to 24 may optionally include presenting the plurality of goal options including at least a goal option of prevention of habituation, and the subject matter of selecting using the processor one or more programmability options associated with the selected one or more goals as found in any one or any combination of Examples 17 to 24 may optionally include selecting the one or more programmability options including at least one of a programmability option of microburst and cycling, a programmability option of program scheduling, or a programmability option of pulse-by-pulse patterning in response to the goal option of prevention of habituation being selected.

In Example 26, the subject matter of presenting the plurality of goal options using the user interface as found in any one or any combination of Examples 17 to 25 may optionally include presenting the plurality of goal options including at least a goal option of providing desynchronizing therapy, and the subject matter of selecting using the processor one or more programmability options associated with the selected one or more goals as found in any one or any combination of Examples 17 to 25 may optionally include selecting the one or more programmability options including at least one of a programmability option of microburst and cycling or a programmability option of pulse-by-pulse patterning in response to the goal option of providing desynchronizing therapy being selected.

In Example 27, the subject matter of presenting the plurality of goal options using the user interface as found in any one or any combination of Examples 17 to 26 may optionally include presenting the plurality of goal options including at least a goal option of plasticity induction, and the subject matter of selecting using the processor one or more programmability options associated with the selected one or more goals as found in any one or any combination of Examples 17 to 26 may optionally include selecting the one or more programmability options including at least one of a programmability option of microburst and cycling or a programmability option of pulse-by-pulse patterning in response to the goal option of plasticity induction being selected.

In Example 28, the subject matter of presenting the plurality of goal options using the user interface as found in any one or any combination of Examples 17 to 26 may optionally include presenting the plurality of goal options including at least a goal option of precision targeting, and the subject matter of selecting using the processor one or more programmability options associated with the selected one or more goals as found in any one or any combination of Examples 17 to 26 may optionally include selecting the one or more programmability options including at least one of a programmability option of wide parameter range, a programmability option of microburst and cycling, or a programmability option of pulse-by-pulse patterning in response to the goal option of precision targeting being selected.

In Example 29, the plurality of goal options as found in any one or any combination of Examples 16 to 22 may optionally include of multi-symptom control, power efficiency, prevention of habituation, providing desynchronizing therapy, plasticity induction, and precision targeting.

In Example 30, the plurality of programmability options as found in Example 29 may optionally include wide parameter range, various stimulation frequency combinations, active recharge options, microburst and cycling, program scheduling, and pulse-by-pulse patterning.

An example (e.g., "Example 31") of a non-transitory computer-readable storage medium including instructions, which when executed by a system, cause the system to perform a method a method for delivering neurostimulation from a stimulation device is also provided. The method may include: receiving one or more goal options selected from a plurality of goal options each including at least one goal for deep brain stimulation (DBS); selecting using the processor one or more programmability options associated with the received one or more goal options a plurality of programmability options each allowing one or more aspects of at least one of the pattern of neurostimulation pulses or the delivery of the neurostimulation according to the pattern of neurostimulation pulses to be programmable; receiving programming information required by the selected one or more programmability options; determining a pattern of neurostimulation pulses for the selected one or more goal options using the received programming information; and generating information for programming the stimulation device to deliver the neurostimulation according to the determined pattern of neurostimulation pulses.

In Example 32, the method as found in Example 31 may optionally include the subject matter of any one or any combination of Examples 17 to 30.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
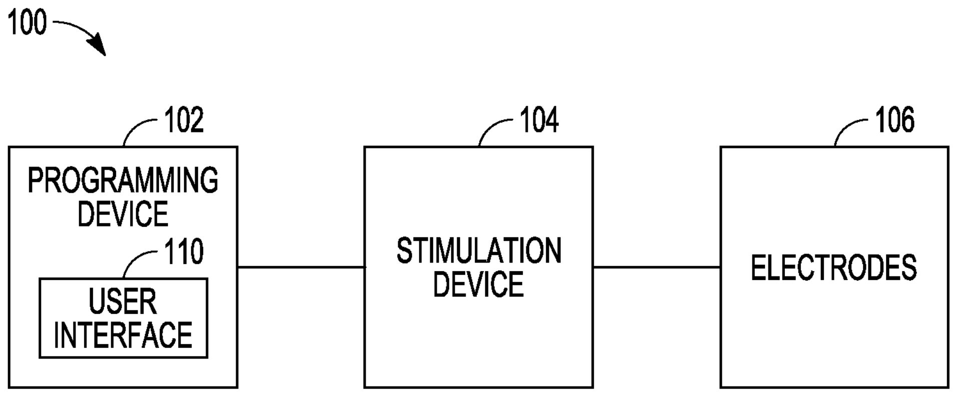
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system and method for delivering deep brain stimulation (DBS) to a patient according a pattern of neurostimulation pulses using a stimulation device and defining the pattern of neurostimulation pulses with variable stimulation waveforms and stimulation fields using a programming device. In various embodiments, the neurostimulation device can be an implantable device that can deliver the neurostimulation pulses to the patient's brain through one or more implantable leads each include multiple electrodes.

Various examples of existing DBS systems delivers a tonic sequence of biphasic electrical pulses each having a stimulation phase following by a passive recharge phase after an interphasic delay. For example, for Parkinson's Disease, chronic stimulation may be applied with pulses of a fixed waveform delivered at 130 Hz pulse rate. Neurostimulation using tonic stimulation pulses of a single waveform have been efficacious in many conditions for well selected movement disorders patients. The limited adjustability of parameters (e.g., number of field-adjustable parameters, range of each field-adjustable parameter) makes the programming for each patient easy. However, disadvantages associated with the limitations in stimulation parameter programmability include, among other things, limited efficacy for some patients, limited efficacy for some symptoms (e.g. axial symptoms), known side effects (e.g. dysarthria or dyskinesias), and insufficient leveraging of fundamental neuroscience knowledge of the brain (e.g., firing patterns under physiological and pathological conditions and responses of the nervous system to more complex spatio-temporal patterns of stimulation). Therefore, there is a need for improving efficacy, reducing side effects, and expanding indications for DBS by providing for the capability of delivering a patterned sequence c, for example with pulse-by-pulse waveform and stimulation field programmability.

The present subject matter provides for programming of such patterned sequences of neurostimulation pulses, as well as for scheduling of their automated delivery, for patients with DBS systems such as those with chronically implanted neurostimulators. In various embodiments, the present subject matter can be implemented within one or more programming devices. In various embodiments, such one or more programming devices can support existing implantable neurostimulators without the need for different implantable neurostimulator hardware and/or firmware. While providing new, advanced programming capabilities, such the one or more programming devices can enforce known and/or existing DBS safety limits (e.g., limit for amount and/or density of charge injected, limit for pulse amplitude). When compared to existing DB S systems delivering tonic stimulation, the present subject matter can be applied to program DBS with patterned sequences of pulses to, among other things, increase therapy efficiency (improved efficacy, reduced side effects, and/or reduced power consumption), prevent habituation (decreased response to neurostimulation), improve neural selectivity, induce neural plasticity, and/or allow for personalized therapy.

FIG. 1 illustrates an embodiment of a neurostimulation system 100.

System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who examiners and/or treats the patient using system 100; and a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for DBS applications. Such DBS configuration includes various features that may simplify the task of the user in programming stimulation device 104 for delivering DBS to the patient, such as the features discussed in this document.

Figure 2:
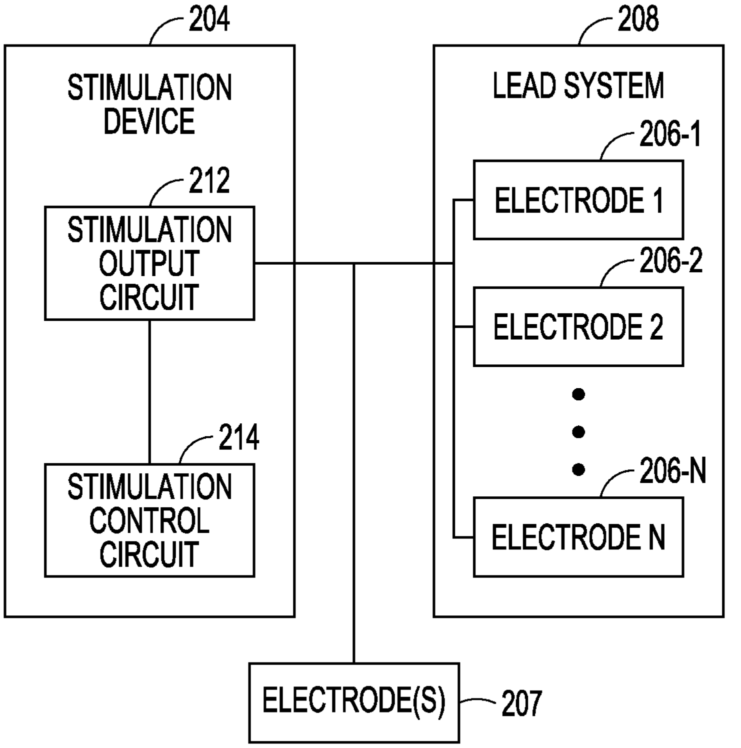
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100.

Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N>2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
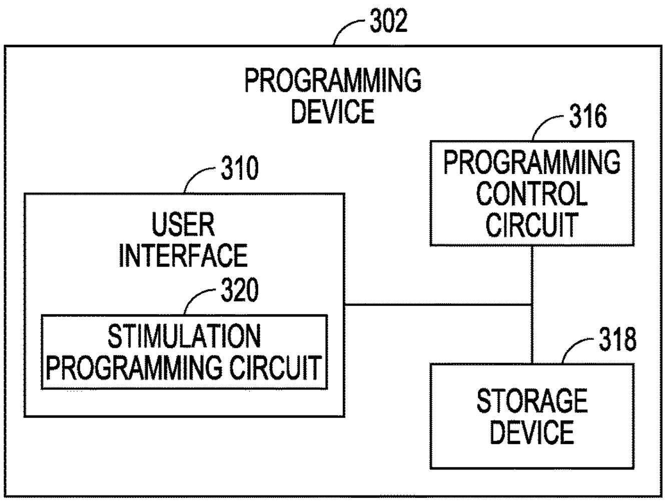
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Programming control circuit 316 generates the plurality of stimulation parameters that controls the delivery of the neurostimulation pulses according to a specified stimulation configuration that can define, for example, stimulation waveform and electrode configuration. User interface 310 represents an embodiment of user interface 110 and includes a stimulation programming circuit 320. Storage device 318 stores information used by programming control circuit 316 and stimulation programming circuit 320, such as information about a stimulation device that relates the stimulation configuration to the plurality of stimulation parameters and information relating the stimulation configuration to a volume of activation in the patient. In various embodiments, stimulation programming circuit 320 can be configured to support one or more functions allowing for programming of stimulation devices, such as stimulation device 104 including its various embodiments as discussed in this document, to control delivery of neurostimulation pulses using stimulation parameters with parameter dithering according to the present subject matter, as further discussed below with reference to FIGS. 9-13.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation configuration" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

Figure 4:
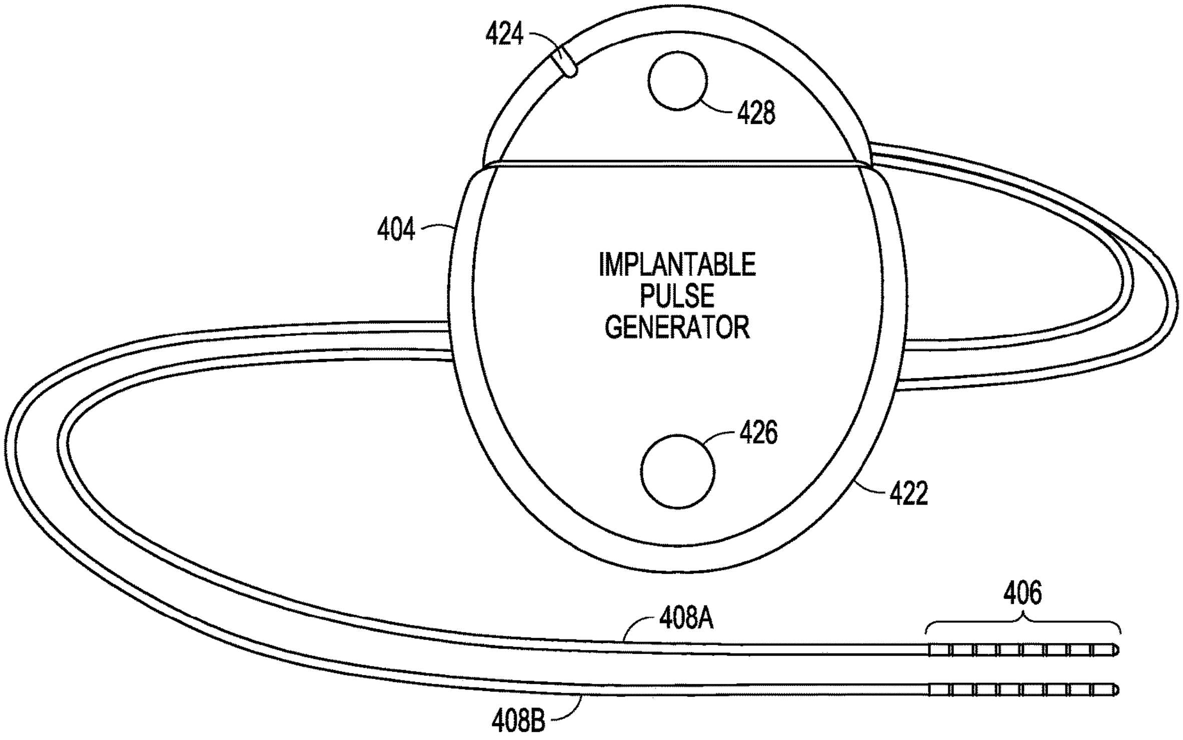
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIGS. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
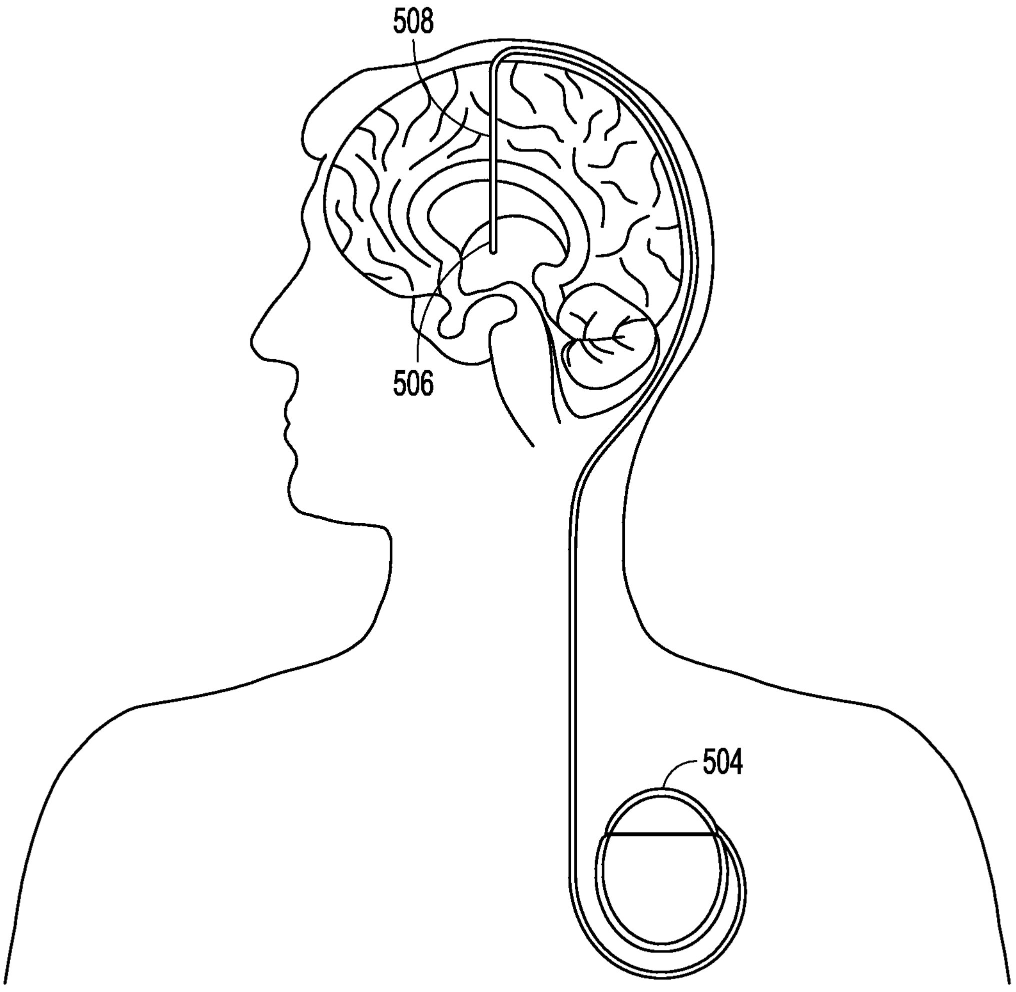
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide DBS to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), globus pallidus externus (GPe), medial forebrain bundle (MFB), periaquaductal gray (PAG), periventricular gray (PVG), habenula, subgenual cingulate cortex, ventral intermediate nucleus (VIM) of the thalamus, anterior nucleus (AN) or other nuclei of the thalamus, zona incerta, ventral capsule, ventral striatum, nucleus accumbens, and other white matter tracts connecting these and other structures.

Returning to FIG. 4, the IPG 404 can include a hermetically-sealed IPG case 422 to house the electronic circuitry of IPG 404. IPG 404 can include an electrode 426 formed on IPG case 422. In some embodiments, IPG case 422 can be used as electrode 426. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
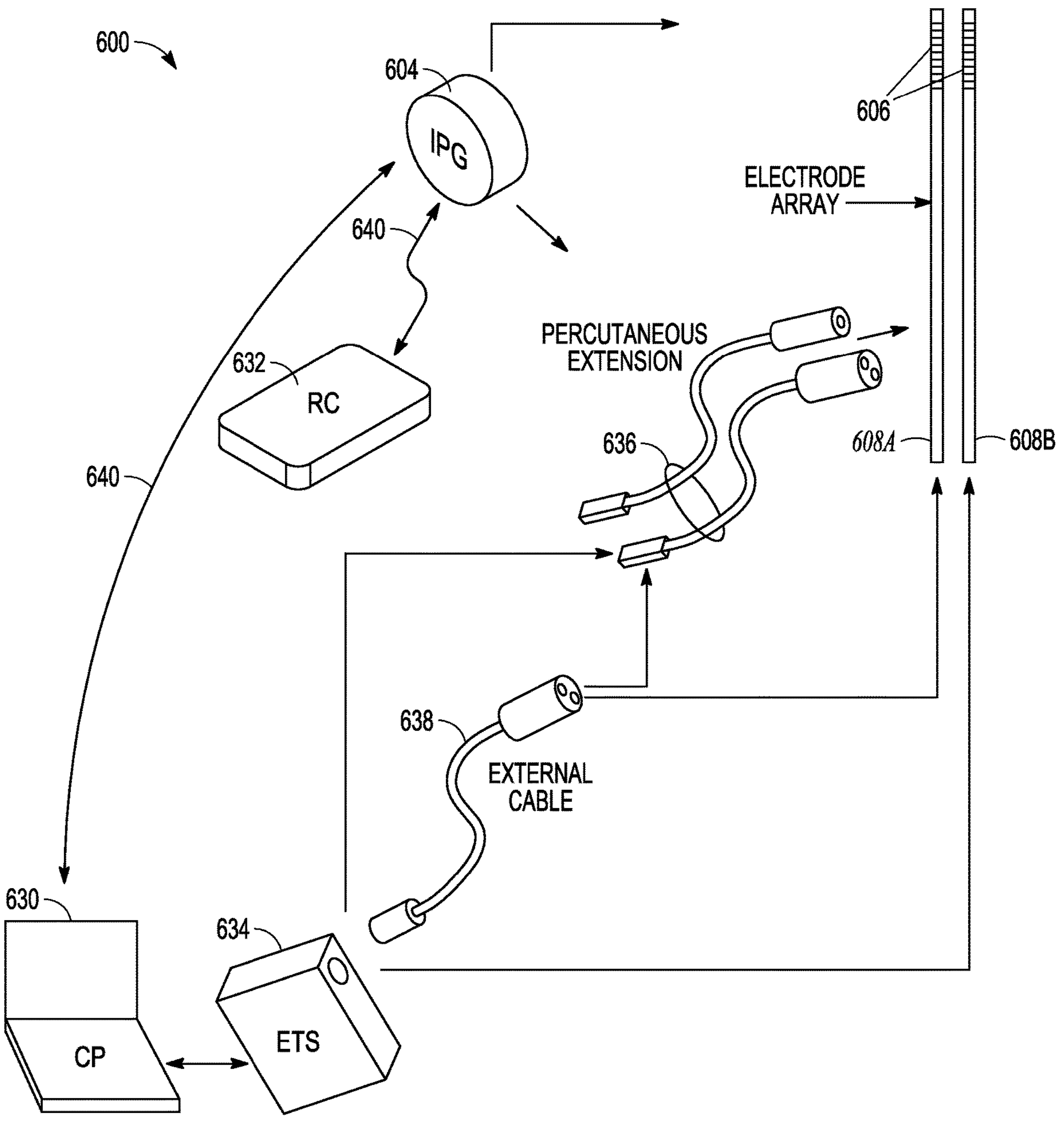
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$, is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link. 10073*j* CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
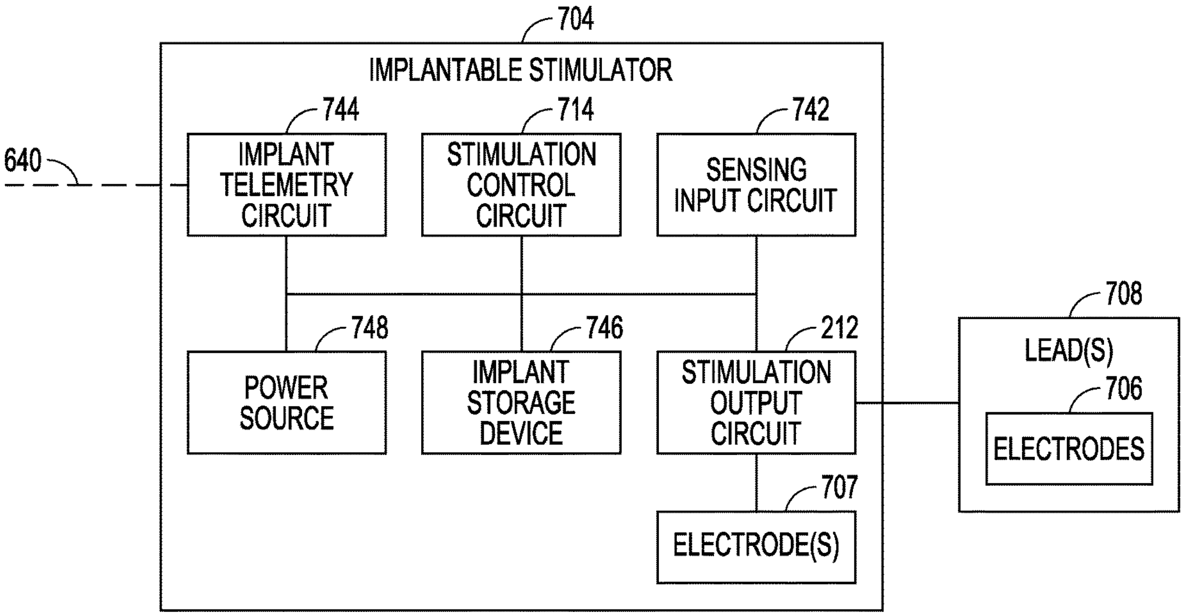
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing input circuit (also known as a sensing circuit) 742 that provides the stimulator with a sensing capability, stimulation output circuit 212, a stimulation control circuit 714, an implant storage device 746, an implant telemetry circuit 744, a power source 748, and one or more electrodes 707. Sensing input circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing input circuit 742.

In various embodiments, sensing input circuit 742, stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
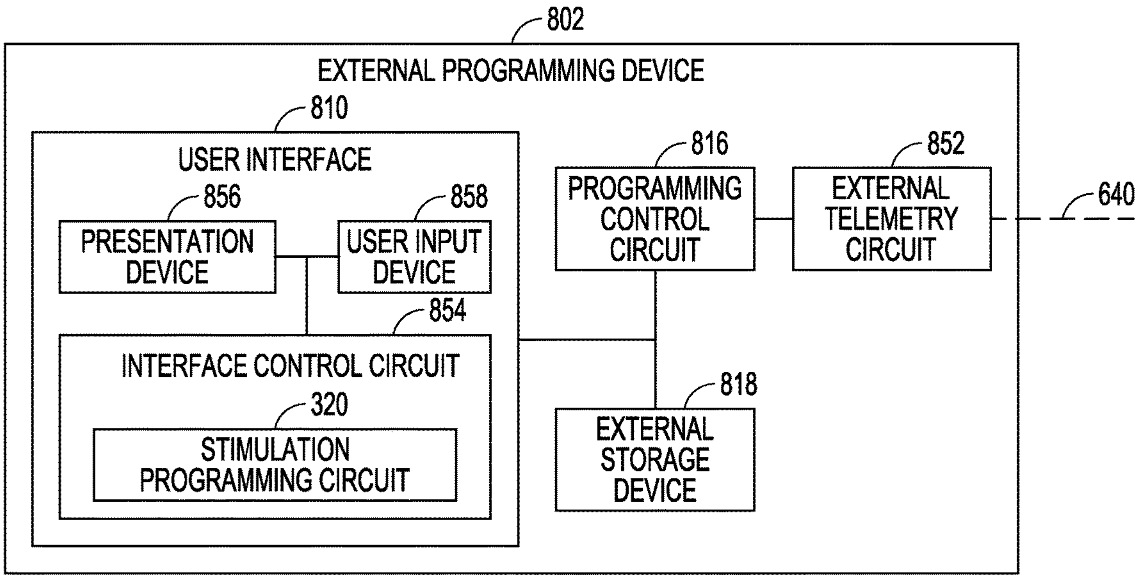
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on a specified stimulation configuration (e.g., the pattern of neurostimulation pulses as represented by one or more stimulation waveforms and one or more stimulation fields, or at least certain aspects of the pattern). The stimulation configuration may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation programming circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figure 9:
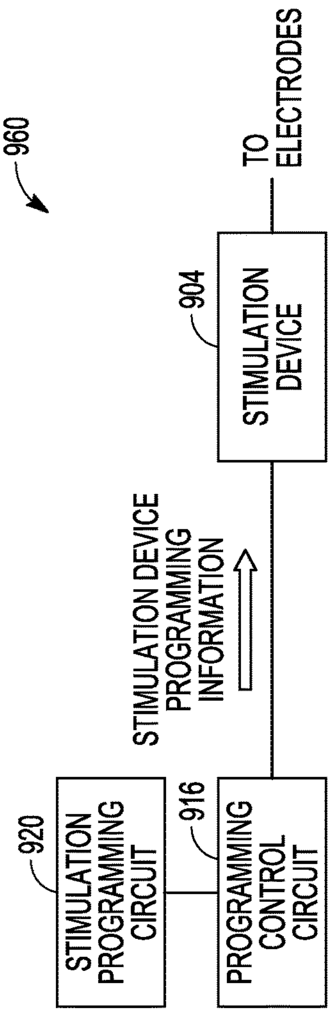
FIG. 9 illustrates an embodiment of a system for delivering deep brain stimulation (DBS).

FIG. 9 illustrates an embodiment of a system 960 for delivering DBS. System 960 can include a stimulation device 904, a programming control circuit 916, and a stimulation programming circuit 920. System 960, including the various embodiments of its components, can be implemented in any suitable neurostimulation systems, including but not limited to those discussed above, such as systems 100 and 600 (including the various embodiments of their components as discussed above). For example, stimulation device 904 can be implemented in stimulation device 104, stimulation device 204, IPG 404, IPG 504, IPG 604, or implantable stimulator 704. Programming control circuit 916 can be implemented in programming control circuit 316 or programming control circuit 816. Stimulation programming circuit 920 can be in implemented in stimulation programming circuit 320. In other words, stimulation device 104, stimulation device 204, IPG 404, IPG 504, IPG 604, or implantable stimulator 704 can be configured to include stimulation device 904, programming control circuit 316 or programming control circuit 816 can be configured to include programming control circuit 916, and stimulation programming circuit 320 can be controlled to include stimulation programming circuit 920.

Stimulation device 904 can be connected to electrodes, such as selected from the electrodes discussed above (e.g., electrodes 106, 206, 207, 406, 422, 426, 428, 506, 606, 706, and 707) and deliver the neurostimulation to a patient using the electrodes. Programming control circuit 916 can represent an example of programming control circuit 316 or 816 and can generate information for programming stimulation device 904 to deliver the neurostimulation according to a pattern of neurostimulation pulses. Stimulation programming circuit 920 can represent an example of stimulation programming circuit 320 and can determine the pattern of neurostimulation pulses. In various embodiments, stimulation programming circuit 320 can determine the pattern of neurostimulation pulses to be applied in a DBS therapy automatically, semi-automatically by interacting with the user, and/or manually based on inputs from the user.

In one embodiment, stimulation programming circuit 920 is configured to receive one or more goal options, to select one or more programmability options associated with the received one or more goal options, to receive programming information required by the selected one or more programmability options, and to determine the pattern of neurostimulation pulses for the selected one or more goal options using the received programming information. The one or more goal options can be selected from a plurality of goal options each including at least one goal for the DBS therapy (e.g., a therapeutic objective, or a device power efficiency). The one or more programmability options can be selected from a plurality of programmability options each allowing one or more aspects (e.g., types and/or value ranges of stimulation parameters) of the pattern of neurostimulation pulses and/or the delivery of the neurostimulation according to the pattern of neurostimulation pulses to be programmable. The receive programming information required by each selected programmability option can include, for example, values of stimulation parameters designated to be programmable under that programmability option.

In various embodiments, stimulation control circuit 916 and stimulation programming circuit 920 are includes in a programming device for programming stimulation device 904. For example, when implantable stimulator 704 is configured to include stimulation device 904, external programming device 802 can be configured for programming control circuit 816 to include programming control circuit 916 and stimulation control circuit 320 to include stimulation control circuit 920. User interface 810 can be configured to include a composer (e.g., using stimulation control circuit 910 functioning with presentation device 856 and user input device 858) to compose one or more patterns of neurostimulation pulses and to schedule delivery of one or more patterns of neurostimulation pulses. Each pattern of neurostimulation pulses, and/or its building blocks, can be edited and/or imported using the composer.

Figure 10:
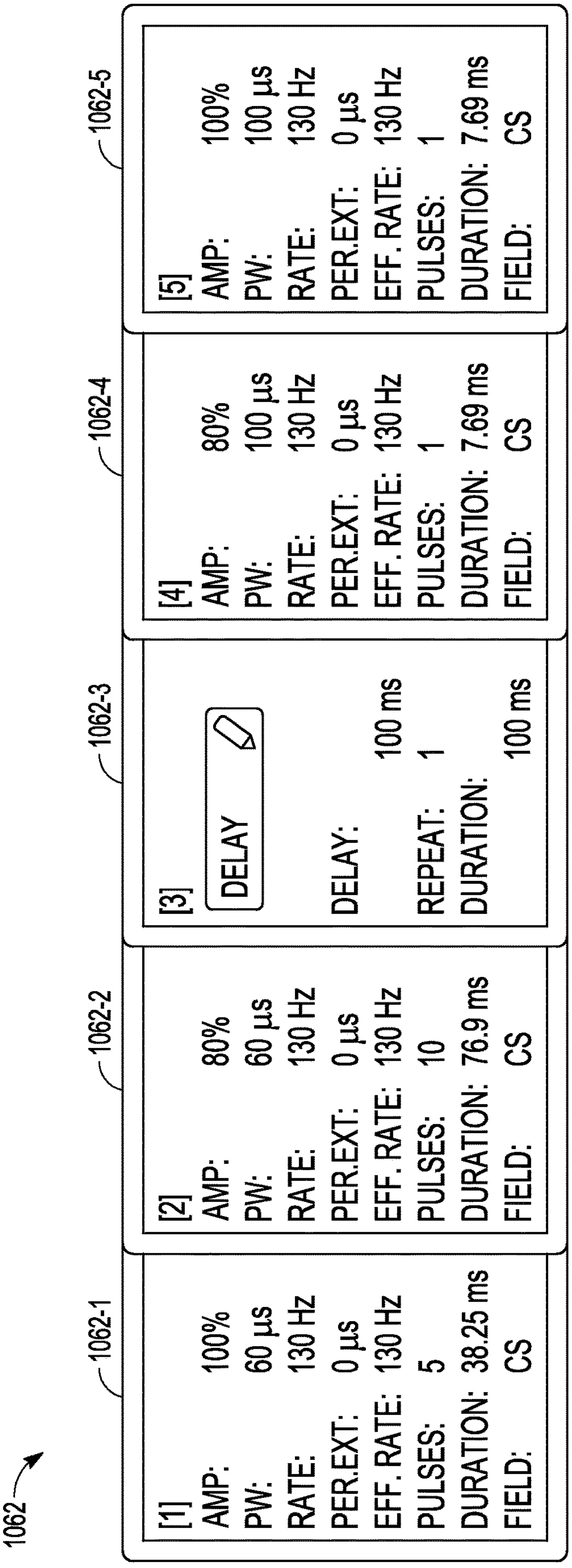
FIG. 10 illustrates an example of a sequence of stimulation and non-stimulation blocks for DBS.

FIG. 10 illustrates an example of a sequence 1062 of stimulation and non-stimulation blocks for DBS. In various embodiments, the pattern of neurostimulation pulses for DBS can be defined by a stimulation program including individually programmable program building blocks. Examples of the individually programmable program building blocks include individually programmable pulses, blocks, and sequences. In the illustrated example, a sequence 1062 includes 5 blocks 1062-1, 1062-2, 1062-3, 1062-4, and 1062-5 each being a stimulation block or a non-stimulation block, as discussed below The individually programmable pulses can each be defined using programmable parameters such as pulse waveform (e.g., monophasic, biphasic, multiphasic, passive recharge, active recharge, or burst), pulse amplitude, pulse width, and/or interphasic interval. The individually programmable blocks can each be a stimulation block during which one or more neurostimulation pulses are delivered (e.g., block 1062-1 or 1062-2 each including multiple pulses, or block 1062-1 or 1062-2 each including one pulse) or a non-stimulation block (e.g., block 1062-3) also referred to as a delay block) during with no pulse is delivered. The stimulation block can be defined using programmable parameters such as pulse amplitude, pulse width, pulse rate, number of pulses or block duration, and/or stimulation field (electrode configuration specifying active electrodes and/or fractionalization). The stimulation blocks can have functions that describe modulation of one or more of the programmable parameters over time. For example, a stimulation block can be defined with a sinusoidal modulation of a pulse amplitude. The non-stimulation block can be defined using a programmable parameter of delay duration (duration of the non-stimulation block). The individually programmable sequences can each include one or more blocks. In various embodiments, a sequence can be composed by creating one or more blocks and/or selecting one or more blocks from stored (pre-configured) and/or imported (e.g., from another system/user) blocks, arrange the blocks in a temporal order (e.g., a random, pseudorandom, or fixed order). The number of successive repetitions of each block in the sequence can be programmable.

The stimulation program for DBS can be composed to include one or more sequences, one or more blocks, and/or one or more pulses arranged in a programmable temporal order. The stimulation program can include one or more sequences and/or other stimulation patterns (e.g., pulses, burst of pulses, blocks) in a random, pseudorandom, or fixed order. One or more stimulation programs can be scheduled to be delivered to the patient as the DBS therapy for the patient. In various embodiment, a neurostimulation system including system 960 can be used to compose the stimulation programs, including their building blocks, and to schedule delivery of neurostimulation according to one or more of the composed stimulation programs for applying the DBS therapy.

Figure 11:
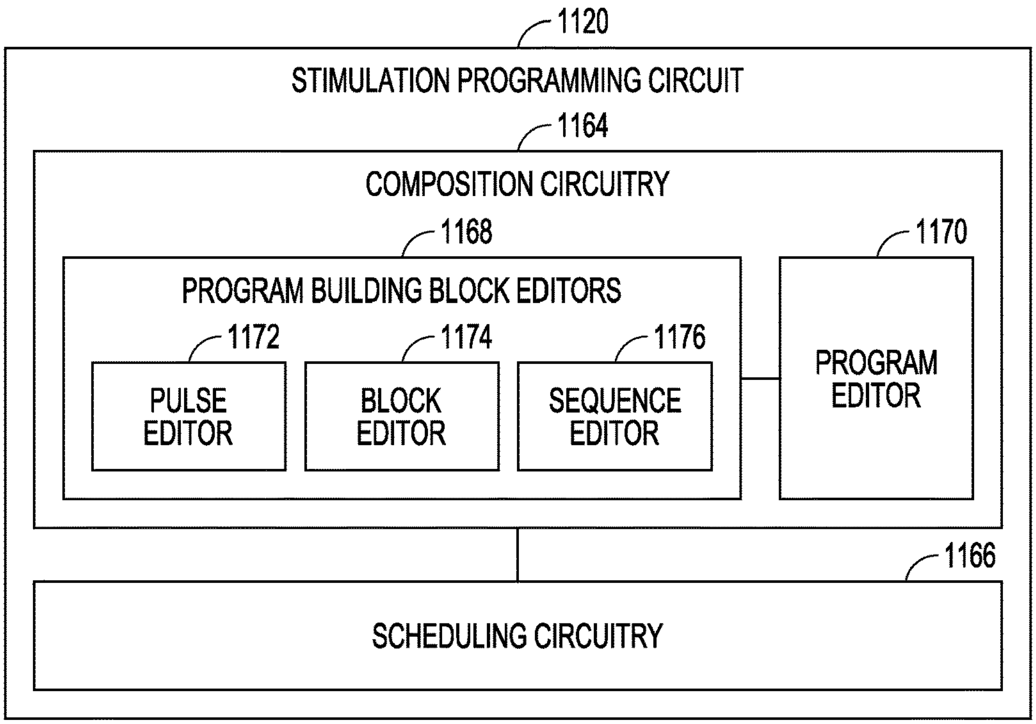
FIG. 11 illustrates an embodiment of a stimulation programming circuit for use in a DBS system, such as the system of FIG. 9.

FIG. 11 illustrates an embodiment of a stimulation programming circuit 1120 for use in a DBS system such as system 960. Stimulation programming circuit 1120 can represent an example of stimulation programming circuit 920 and can include composition circuitry 1164 and scheduling circuitry 1166.

Composition circuitry (also referred to as composer) 1164 can compose a pattern of neurostimulation pulses, including one or more programs and program building blocks (e.g., pulses, blocks, and/or sequences). Scheduling circuitry 1166 can schedule delivery of neurostimulation according to the composed pattern (e.g., one or more programs) of neurostimulation pulses. In various embodiments, composition circuitry 1164 and scheduling circuitry 1166 operate with a presentation device (e.g., presentation device 856) and a user input device (e.g., user input device 858) to allow for user control in the composition of the pattern of neurostimulation pulses. Composition circuitry 1164 includes program building block editors 1168 for creating, editing, and/or importing each building block of a stimulation program and a program editor 1170 for creating, editing, and/or importing the stimulation program. In the illustrated embodiment, program building block editors 1168 a pulse editor 1172 for creating, editing, and/or importing each pulse, a block editor 1174 for creating, editing, and/or importing each block, and a sequence editor 1176 for creating, editing, and/or importing each sequence. Program editor 1170 can create each program using various combination of the created, edited, and/or imported program building blocks arranged in a temporal order according to which the neurostimulation is to be delivered.

In various embodiments, composition circuitry 1164 can provide one or more programmability options for one or more goal options. The one or more programmability options each allow one or more aspects of the pattern of neurostimulation pulses to be programmable. Example of such one or more aspects includes type and value range of a stimulation parameter that is designated to be programmable. Each programmability option requires programming information for setting the relevant stimulation parameters. In various embodiments, composition circuitry 1164 can determine the programming information for each selected programmability option manually, semi-automatically, and/or automatically. Composition circuitry 1164 can present parameters on the presentation device and receives values for these parameters manually entered by the user. Composition circuitry 1164 can also present programming guidance, such as values of a parameter to be selected from a list (e.g., a pull-down menu), recommended values for the parameter, and/or a recommended value range for the parameter, using the presentation device. Composition circuitry 1164 can also automatically generate recommended values for all the parameters to be programmed under the selected programmability option and can optionally present these values using the presentation device to the user for determining whether to accept or modify the recommended values. The one or more goal options each include an intended effect of delivering the neurostimulation according to the pattern of neurostimulation pulses. Examples of such one or more goal options include therapeutic effects to be achieved, therapy types to be supported, and device performance objectives. Examples of programmability options and goal options, as well as their relations, provided and used by composition circuitry 1164 are further discussed below, with reference to FIG. 12.

In various embodiments, circuits of systems 100, 600, and 960, including their various embodiments and various embodiments of their components discussed in this document, may be implemented using a combination of hardware and software. For example, the circuit of user interface 110, stimulation output circuit 212, stimulation control circuit 214, programming control circuit 316, stimulation programming circuit 320, sensing circuit 742, stimulation control circuit 714, implant telemetry circuit 744, external telemetry circuit 852, programming control circuit 816, interface control circuit 854, the circuit of stimulation 904, programming control circuit 916, stimulation programming circuit 920, and stimulation programming circuit 1120 may each be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 12:
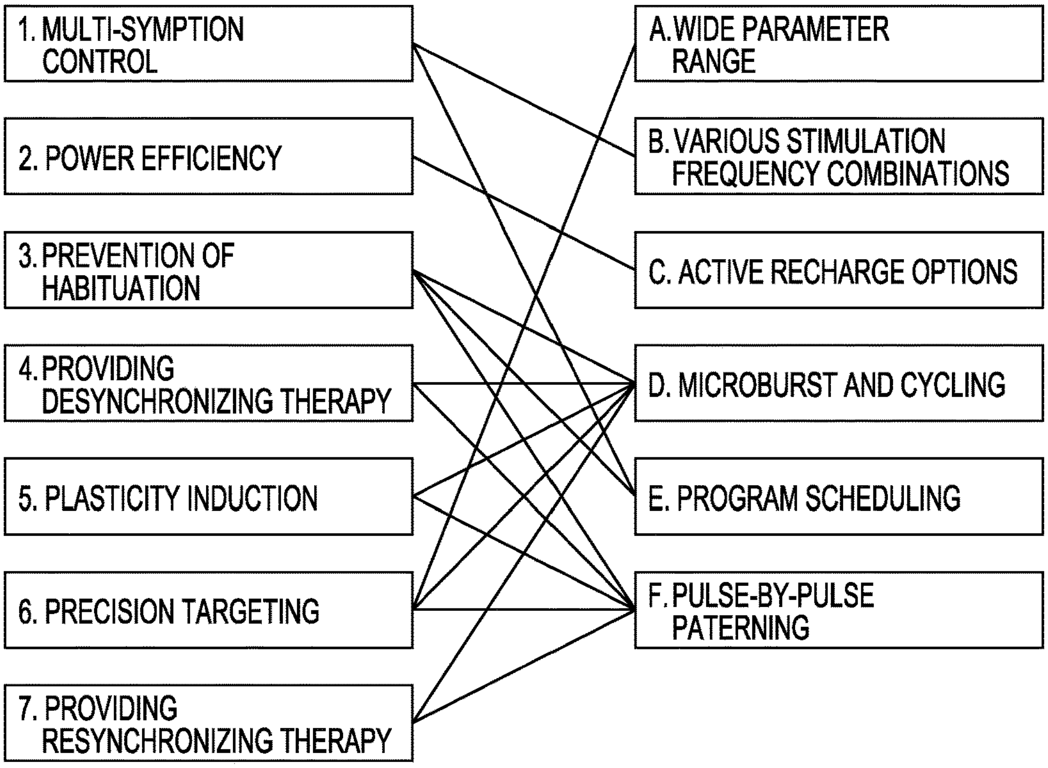
FIG. 12 illustrates an embodiment of a relationship between goal options and programmability options for use in a DBS system, such as the system of FIG. 9.

FIG. 12 illustrates an embodiment of a relationship between goal options and programmability options for use in a DBS system, such as system 960. A list of programmability options, a list of goal options, and a mapping relationship between the programmability options and the goal options are shown, by way of example, but not by way of restriction, for illustrative purposes. The list of programmability options includes:

A. wide parameter range;
B. various stimulation frequency combinations (e.g., different frequencies or frequency ranges for pulses delivered to different stimulation fields for different neural target areas);
C. active recharge options;
D. microburst and cycling;
E. program scheduling; and
F. pulse-by-pulse patterning.

The list of goal options (with relationship to the programmability options noted) includes:

1. multi-symptom control (using programmability options B and/or E);
2. power efficiency (using programmability option C);
3. prevention of habituation (using programmability options D, E, and/or F);
4. providing desynchronizing therapy (using programmability options D and/or F);
5. plasticity induction (using programmability options D and/or F);
6. precision targeting (using programmability options A, D, and/or F); and
7. providing resynchronizing therapy (using programmability options D and/or F).

In various embodiments, composition circuitry 1164 can determine the pattern of neurostimulation pulses for one or more goal options selected from the goal options 1-6 (and/or the like) using programming information required by one or more programmability options selected from the programmability options A-F (and/or the like). Composition circuitry 1164 can also enforce various DBS safety rules during the determination of the pattern of neurostimulation pulses, for example by limiting an amount or density of charge injected to tissue of the patient by a pulse, a block, a sequence, a program, or a specified time period.

In various embodiments, composition circuitry 1164 can receive the patient's symptoms and one or more goal options from the user (e.g., by selecting from the goal options 1-6 above) and generate a recommendation on which programming option(s) to provide (e.g., selecting from the programmability options A-F above) by using a map (e.g., the mapping relationship shown in FIG. 12 and with the goal options 1-6). In one embodiment, composition circuitry 1164 is configured to:

- present a list (e.g., a drop-down menu) of goal options (e.g., the goal options 1-6 or the like) using the presentation device;
- receive user selection of one or more goal options from the presented list of goal options using the user input device;
- present a list (e.g., another drop-down menu) of one or more programmable options based on the selected one or more goal options (e.g., selected from programmability options A-F or the like) using the presentation device;
- receive user selection of one or more programmable options using the user input device;
- present request for programming information (e.g., parameter fields allowing the user to set values) based on the selected one or more programmable options using the presentation device;
- receive the requested programming information using the user input device; and
- generate a sequence or a program automatically based on the selected one or more goals, the selected one or more programmable options, and the programming information.

In various embodiments, composition circuitry 1164 can receive more information, such as the patient's symptoms or other patient-specific information, in addition to the selected one or more goal options. Composition circuitry 1164 can also receive device information, such as information specific to the stimulation device to be programmed, in additional to the programmability options. In one embodiment, composition circuitry 1164 employs artificial intelligence to execute an algorithm to determine the programming information (including programming information to be obtained from the user) based on all the received information and compose the pattern of neurostimulation pulses accordingly.

Programmability options A-F and goal options 1-6 that are supported by system 960 are discussed as examples below. More examples of programmability options and goal options will likely become available, for example, as results of using addition findings from research and development related to DBS. Programmability options A-F are discussed as examples as follows:

A. Wide Parameter Range. A wide range of adjustable stimulation parameters, including their types and/or values, is provided for defining the pattern of neurostimulation pulses. This range is substantially expanded from that of existing tonic stimulation. In an example, higher pulse frequencies and/or longer pulse widths are allowed, such as a pulse frequency range of about 2-1200 Hz and a pulse width range of about 10-1000 ns. In another example, the pulse frequency can be set to about 100 kHz or higher. The resolution of the pulse frequency may be increased, especially to afford precise pulse timing within and across sites of stimulation.

B. Various Stimulation Frequency Combinations. The pattern of neurostimulation pulses (e.g., a sequence or program) can include a pulse frequency that changes over time during the pattern and/or different pulse frequencies for pulses delivered to different stimulation fields. The pulse frequency can be programmable for each block as a constant (so it does not vary within the block) or as a function of time (so it can vary within the block). Different pulse frequencies can be applied alternatingly and/or simultaneously to the pulses delivered to the different stimulation fields.

C. Active Recharge Options. Various recharge schemes including active and/or passive recharge phases can be applied to the pattern of neurostimulation for charge balancing. A recharge scheme (defining how recharge phases are arranged relative to stimulation phases in a stimulation waveform) can be selected for reduction of power consumption of the stimulation device (e.g., a battery-powered implantable neurostimulator), for additional therapeutic benefits, and/or for other effects. The recharge schemes can include symmetric active recharge, where the pulse widths and amplitudes of opposite polarities are equal, and asymmetric active recharge, particularly where the recharge phase has a lower amplitude and longer pulse width. The recharge schemes can include pulse phase polarities designed to bring a particular circuit property toward or to zero, such as an interface potential or a total net charge delivered. Active and passive recharge pulses can be interspersed, and charge-recovery schemes can seek a goal such as zero-balance in a pairwise fashion, or given some longer series of pulses or pulse phases (e.g., every 3, 7, 100, or other number of pulses or phases). A particular recharge scheme may allow for the neurostimulation to achieve an intended outcome with fewer pulses and/or reduced pulse amplitude. Periods of non-stimulation during recharge may be tolerable or, in some cases, desirable for therapeutic effects (e.g., neural plasticity induced long-lasting reduction of symptoms). Stimulation (e.g., cathodic) and recharge (e.g., anodic) phases of a stimulation waveform may activate different neural elements, so both phases may contribute to the overall therapeutic effect.

Examples of the various recharge schemes include:

- a burst of neurostimulation pulses with only stimulation phases, followed by a long active or passive recharge pulse (e.g., 10 cathodic stimulation pulses at followed by a long anodic recharge pulse, or 10 anodic stimulation pulses at followed by a long cathodic recharge pulse);
- a burst of neurostimulation pulses with only stimulation phases, followed a burst of symmetric active recharge pulses (e.g., 10 cathodic stimulation pulses followed by 10 anodic recharge pulses, or 10 anodic stimulation pulses followed by 10 cathodic recharge pulses);
- a burst of neurostimulation pulses with only stimulation phases preceded by a recharge pulse ("pre-pulsing") and followed by another recharge pulse ("post-pulsing"); and
- a burst of neurostimulation pulses at VHF with only stimulation phases, followed by an active recharge pulse and a passive recharge pulse (the active recharge pulse and then the passive recharge pulse, or the passive recharge pulse and then the active recharge pulse).

Various examples of recharging schemes and timing are discussed in U.S. Pat. No. 10,994,143 B2, assigned to Boston Scientific Neuromodulation Corporation, which is incorporated by reference herein in its entirety.

D. Microburst and Cycling. The pattern of neurostimulation pulses can include a series of stimulation blocks each defining a burst of pulses ("microburst") at a programmable frequency, and optionally non-stimulation (delay) blocks, in a fixed, pseudorandom, or random order. The burst is also referred to as a microburst, particularly when the burst duration is very short, such as during very high frequency neurostimulation in which the pulse frequency can be 100 kHz or above. The series of stimulation blocks can be repeated (cycling) for a programmable duration or number of repetitions. Each block can be repeated within the series of stimulation blocks with the number of repetitions programmable. Such microburst and cycling can be applied, for example, to selectively activate certain cell types.

E. Program Scheduling. A DBS therapy session can be scheduled with automatically timed delivery of selected one or more stimulation programs over a programmable session duration (e.g., between 10 seconds to 7 days). Each stimulation program can include tonic and/or patterned stimulation, delivered to one or more stimulation fields. In one example of a DBS therapy session, stimulation program 1 is scheduled to be delivered for 22 hours/day (e.g., 2 am to 12 am) with tonic stimulation to an area A of the patient, and stimulation program 2 is scheduled to be delivered for 2 hours/day (e.g., 12 am to 2 am) with tonic stimulation to the area A and bursting stimulation in an area B of the patient. This DBS therapy session scheduling results in constant tonic stimulation for a day and 2 hours of simultaneous tonic and bursting stimulations for that day.

F. Pulse-by-Pulse Patterning. The pattern of neurostimulation can be composed on a pulse-by-pulse basis. Examples of the composition using pulse-by-pulse patterning capability include:

- coordinated reset, with examples of coordinated reset with 3 stimulation fields, each defined by a set of electrodes and/or fractionalization, including:
  - (a) repeating in the following order: delivering a burst to stimulation field 1, introducing a fixed inter-burst delay, delivering a burst to stimulation field 2, introducing the inter-burst delay, delivering a burst to stimulation field 3, introducing the inter-burst fixed delay;
  - (b) same as (a) but with the temporal order of the stimulation fields 1-3 randomized;
  - (c) same as (a) but with the timing between the bursts jittered; and
  - (d) same as (a) but with the timing randomized, with the inter-burst delays selected from a particular distribution;
- paired pulse stimulation across sites to modify connectivity, by controlling timing between delivery of neurostimulation pulses at two different stimulation sites, e.g., a pulse delivered to site 1 with a specific temporal relationship to a pulse delivered to site 2 (e.g., site 1 stimulated 150 ms before site 2), to increase or decrease strength of synaptic connectivity between site 1 and site 2;
- noise patterns, with inter-pulse intervals and/or inter-burst intervals selected from a probability distribution; and
- modulations of pulse parameters, with stimulation parameters (e.g., pulse amplitude, pulse width, pulse frequency) programmable as a function of time using a modulating function (examples discussed in U.S. Pat. No. 9,802,052, assigned to Boston Scientific Neuromodulation Corporation, which is incorporated by reference herein in its entirety.

The programmability options A-F provide for composition of the pattern of neurostimulation pulses for the goal options 1-6. Goal options 1-6 are discussed as examples as follows:

1. Multi-Symptom Control. Multi-symptom control can be achieved using a complex pattern of neurostimulation pulses that can be composed using programmability options B and/or E. The multi-symptom control can be applied to improve therapeutic outcomes for existing indications (e.g., Parkinson's disease and other movement disorders, chronic pain) and/or to allow for new indications (e.g., stroke, Alzheimer's disease, epilepsy, chronic pain, autonomic dysfunction). The complex pattern of neurostimulation pulses can also be customizable for individual patients and/or indications using programmability options B and/or E. In various embodiments, the multi-symptom control can include avoidance of one or more side effects.

2. Power Efficiency. Power efficiency is important for operating the stimulation device, particularly when the stimulation device is a battery powered implantable neurostimulator. Programmability C can be used to increase power efficiency under certain circumstances. For example, active recharge may save battery energy, as compared to passive recharge, by potentially achieving the same therapeutic effect at a reduced pulse amplitude, though this may need to be weighed against additional energy required for actively recharge.

3. Prevention of Habituation. Prolonged tonic stimulation or stimulation with a periodic waveform may cause habituation, when the patient's body stops responding to the neurostimulation at a neuronal level or at a systemic level. Regaining therapeutic effectiveness after habituation occurs generally requires therapy adjustments beyond increasing the amplitude of neurostimulation. Habituation can be prevented by composing and delivering the pattern of neurostimulation without tonic stimulation or stimulation with a periodic waveform using programmability options D, E, and/or F.

4. Providing Desynchronizing Therapy. Providing desynchronizing therapy includes applying DBS to disrupt (potentially pathological) coordination between different neurons. Examples of indications for the desynchronizing therapy include Parkinson's disease, essential tremor, and chronic pain. The pattern of neurostimulation pulses for providing the desynchronizing therapy can be composed using programmability options D and/or F.

5. Plasticity Induction. Neural plasticity to be induced by DBS can include reorganization of neural structure, connectivity, and/or functions. An example indication for the plasticity induction is stroke. The pattern of neurostimulation pulses for the plasticity induction using DBS can be composed using programmability options D and/or F.

6. Precision Targeting. Stimulation fields (electrode configuration, e.g., selection of active electrodes and/or fractionalization) can be programmable for each pulse, block, or sequence to precisely control volumes of activation relative to anatomical structures targeted for delivering DBS for maximizing intended therapeutic effects while minimizing potential side effects. Such precision targeting can be achieved by composing the pattern of neurostimulation pulses (including stimulation waveforms and stimulation fields) using programmability options A, D, and/or F.

7. Providing Resynchronizing Therapy. Providing resynchronizing therapy includes applying DBS to enhance (potentially pathological) lack of coordination between different neurons. Examples of indications for the resynchronizing therapy include schizophrenia, autism, and Alzheimer's disease. The pattern of neurostimulation pulses for providing the resynchronizing therapy can be composed using programmability options D and/or F.

Figure 13:
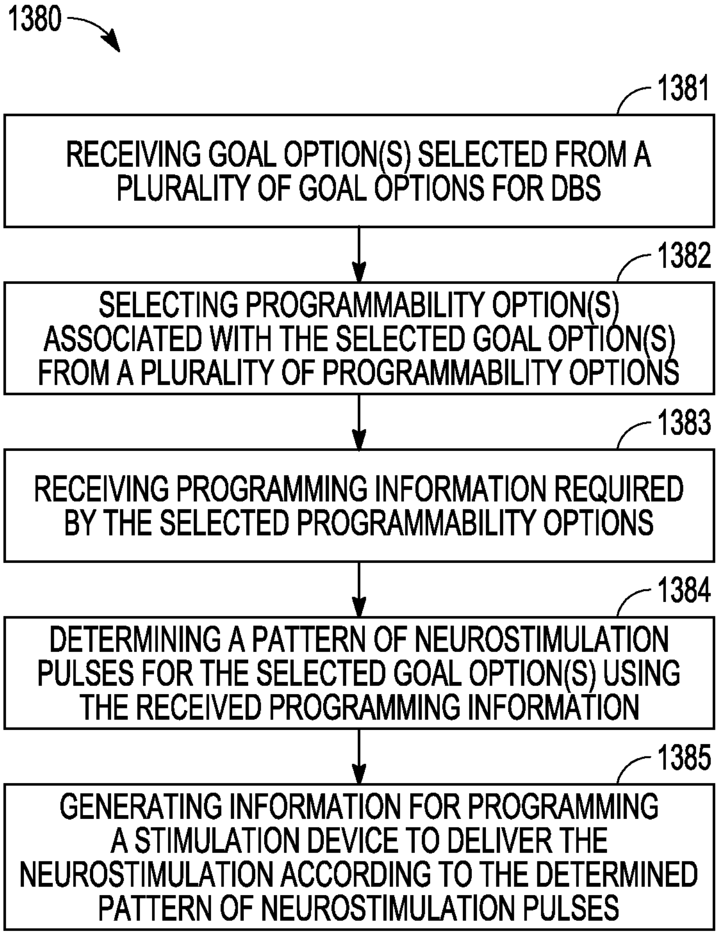
FIG. 13 illustrates an embodiment of a method for controlling delivery of deep brain stimulation (DBS).

FIG. 13 illustrates an embodiment of a method 1380 for controlling delivery of DBS to a patient. Method 1380 can be performed to deliver neurostimulation from a stimulation device according a pattern of neurostimulation pulses using system 960 when system 960 is implemented in a neurostimulation system such as system 100 or 600, including the various embodiments of their components as discussed in this document. In various embodiments, method 1380 is performed using a processor of system 960, such as a processor configured to include at least portions of programming control circuit 916 and stimulation programming circuit 920. In various embodiments, a non-transitory computer-readable storage medium includes instructions, which when executed by a system (e.g., system 960), cause the system to perform method 1380. Examples of such storage medium include external storage device 818, any storage medium used for configuring (e.g., programming) an implantable stimulator (e.g., implantable stimulator 704) and/or external programming device (e.g., external programming device 802), or any combination of these storage media.

At 1381, one or more goal options are selected from a plurality of goal options for DBS. Examples of the goal options include goal options 1-6 discussed above with reference to FIG. 12. In one embodiment, the plurality of goal options is presented using a user interface, and a user selection of the one or more goal options from the plurality of goal options is received using the user interface.

At 1382, one or more programmability options associated with the received one or more goal options are selected from a plurality of programmability options using a mapping relationship between the plurality of goal options and the plurality of programmability options. The programmability options each allow one or more aspects of at least one of the pattern of neurostimulation pulses or the delivery of the neurostimulation according to the pattern of neurostimulation pulses to be programmable. Examples of the programmability options include programmability options A-F discussed above with reference to FIG. 12. An example of the mapping relationship between the plurality of goal options and the plurality of programmability options is the mapping relationship between goal options 1-6 and programmability options A-F discussed above with reference to FIG. 12.

At 1383, programming information required by the selected one or more programmability options is received. Such information can include, for example, values for one or more stimulation parameters designated to be programmable under the selected one or more programmability options.

At 1384, the pattern of neurostimulation pulses for the selected one or more goal options is determined using the received programming information. In one embodiment, the selected one or more programmability options are presented using the user interface, and user input related to at least a portion of the programming information required by the selected one or more programmability options is received using the user interface. In one embodiment, the pattern of neurostimulation pulses is determined by composing a stimulation program and/or program building blocks of the stimulation program using the received programming information. The stimulation program includes stimulation parameters defining the pattern of neurostimulation pulses. The program building blocks each include a subset of the stimulation parameters defining a segment of the pattern of neurostimulation pulses. In one embodiment, the program building blocks include pulses, blocks, and sequences. The pulses are each a pulse of the pattern of neurostimulation pulses. The blocks are each a stimulation block during which pulses of the pattern of neurostimulation pulses are to be delivered or a non-stimulation blocks during which no pulse of the pattern of neurostimulation pulses is to be delivered. The sequences each include multiple blocks of the blocks. In one embodiment, stimulation parameters associated with each programmability option of the selected one or more programmability options are determined using the user interface. This can include presenting values or a value range for each stimulation parameter using the user interface and receiving a value selected from the presented values or a value within the presented value range using the user interface. In one embodiment, applications of the stimulation program for controlling the delivery of the pattern of neurostimulation pulses is scheduled.

At 1385, information for programming the stimulation device to deliver the neurostimulation according to the determined pattern of neurostimulation pulses is generated. The information can be transmitted to the stimulation device to cause the stimulation device to deliver the neurostimulation to the patient according to the determined pattern of neurostimulation pulses.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation from a stimulation device, the system comprising:
- a programming control circuit configured to generate information for programming the stimulation device to deliver the neurostimulation according to a pattern of neurostimulation pulses; and
- a stimulation programming circuit configured to:
  - receive one or more goal options selected from a plurality of goal options each including at least one goal for deep brain stimulation (DBS);
  - select one or more programmability options associated with the received one or more goal options from a plurality of programmability options based on a predetermined relationship mapping each goal option of the plurality of goal options to one or more programmability options of the plurality of programmability options, the programmability options each allowing one or more aspects of at least one of the pattern of neurostimulation pulses or the delivery of the neurostimulation according to the pattern of neurostimulation pulses to be programmable;
  - receive programming information required by the selected one or more programmability options; and
  - determine the pattern of neurostimulation pulses for the selected one or more goal options using the received programming information.

2. The system of claim 1, further including a user interface including a presentation device, a user input device, and the stimulation programming circuit, wherein the stimulation programming circuit is configured to:
- present the plurality of goal options using the presentation device;
- receive a user selection of the one or more goal options from the plurality of goal options using the user input device;
- present the selected one or more programmability options using the presentation device; and
- receive at least a portion of the programming information required by the selected one or more programmability options using the user input device.

3. The system of claim 2, wherein the stimulation programming circuit is configured to allow for:

composition of a stimulation program using the received programming information, the stimulation program including stimulation parameters defining the pattern of neurostimulation pulses; and composition of program building blocks of the stimulation program, the program building blocks each including a subset of the stimulation parameters defining a segment of the pattern of neurostimulation pulses.

4. The system of claim 3, wherein the stimulation programming circuit is configured to determine stimulation parameters associated with each programmability option of the selected one or more programmability options using the presentation device and the user input device.

5. The system of claim 2, wherein the stimulation programming circuit is configured to:

present the plurality of goal options including at least one of multi-symptom control, power efficiency, prevention of habituation, providing desynchronizing therapy, plasticity induction, precision targeting, or providing resynchronizing therapy; and select the one or more programmability options including at least one of wide parameter range, various stimulation frequency combinations, active recharge options, microburst and cycling, program scheduling, or pulse-by-pulse patterning.

6. A method for delivering neurostimulation from a stimulation device, the method comprising:

receiving by a processor one or more goal options selected from a plurality of goal options for deep brain stimulation (DBS);

selecting using the processor one or more programmability options associated with the received one or more goal options from a plurality of programmability options based on a predetermined relationship mapping each goal option of the plurality of goal options to one or more programmability options of the plurality of programmability options, the programmability options each allowing one or more aspects of at least one of a pattern of neurostimulation pulses or the delivery of the neurostimulation according to the pattern of neurostimulation pulses to be programmable;

receiving by the processor programming information required by the selected one or more programmability options;

determining using the processor the pattern of neurostimulation pulses for the selected one or more goal options using the received programming information; and generating information using the processor for programming the stimulation device to deliver the neurostimulation according to the determined pattern of neurostimulation pulses.

7. The method of claim 6, wherein determining using the processor the pattern of neurostimulation pulses comprises composing at least one of a stimulation program or building blocks of the stimulation program using the received programming information, the stimulation program including stimulation parameters defining the pattern of neurostimulation pulses, the program building blocks each including a subset of the stimulation parameters defining a segment of the pattern of neurostimulation pulses.

8. The method of claim 7, wherein composing the program building blocks comprises composing one or more of pulses, blocks, or sequences of the program building blocks, the pulses each being a pulse of the pattern of neurostimulation pulses, the blocks each being a stimulation block during which pulses of the pattern of neurostimulation pulses are to be delivered or a non-stimulation block during which no pulse of the pattern of neurostimulation pulses is to be delivered, the sequence each including multiple blocks of the blocks.

9. The method of claim 7, wherein determining using the processor the pattern of neurostimulation pulses further comprises scheduling of applications of the stimulation program for controlling the delivery of the pattern of neurostimulation pulses.

10. The method of claim 6, wherein:

receiving by the processor the one or more goal options comprises presenting the plurality of goal options using a user interface and receiving a user selection of the one or more goal options from the plurality of goal options using the user interface, and receiving by the processor programming information required by the selected one or more programmability options comprises presenting the selected one or more programmability options using the user interface and receiving user input related to at least a portion of the programming information required by the selected one or more programmability options using the user interface.

11. The method of claim 10, wherein determining using the processor the pattern of neurostimulation pulses further comprises determining stimulation parameters associated with each programmability option of the selected one or more programmability options using the user interface.

12. The method of claim 10, wherein:

presenting the plurality of goal options using the user interface comprises presenting the plurality of goal options including at least a goal option of multi-symptom control; and selecting using the processor one or more programmability options associated with the selected one or more goals comprises selecting the one or more programmability options including at least one of a programmability option of various stimulation frequency combinations or a programmability option of program scheduling in response to the goal option of multi-symptom control being selected.

13. The method of claim 10, wherein:

presenting the plurality of goal options using the user interface comprises presenting the plurality of goal options including at least a goal option of power efficiency; and selecting using the processor one or more programmability options associated with the selected one or more goals comprises selecting the one or more programmability options including at least a programmability option of active recharge options in response to the goal option of multi-symptom control being selected.

14. The method of claim 10, wherein:

presenting the plurality of goal options using the user interface comprises presenting the plurality of goal options including at least a goal option of prevention of habituation; and selecting using the processor one or more programmability options associated with the selected one or more goals comprises selecting the one or more programmability options including at least one of a programmability option of microburst and cycling, a programmability option of program scheduling, or a programmability option of pulse-by-pulse patterning in response to the goal option of prevention of habituation being selected.

15. The method of claim 10, wherein:

presenting the plurality of goal options using the user interface comprises presenting the plurality of goal options including at least a goal option of providing desynchronizing therapy; and selecting using the processor one or more programmability options associated with the selected one or more goals comprises selecting the one or more programmability options including at least one of a programmability option of microburst and cycling or a programmability option of pulse-by-pulse patterning in response to the goal option of providing desynchronizing therapy being selected.

16. The method of claim 10, wherein:

presenting the plurality of goal options using the user interface comprises presenting the plurality of goal options including at least a goal option of plasticity induction; and selecting using the processor one or more programmability options associated with the selected one or more goals comprises selecting the one or more programmability options including at least one of a programmability option of microburst and cycling or a programmability option of pulse-by-pulse patterning in response to the goal option of plasticity induction being selected.

17. The method of claim 10, wherein:

presenting the plurality of goal options using the user interface comprises presenting the plurality of goal options including at least a goal option of precision targeting; and selecting using the processor one or more programmability options associated with the selected one or more goals comprises selecting the one or more programmability options including at least one of a programmability option of wide parameter range, a programmability option of microburst and cycling, or a programmability option of pulse-by-pulse patterning in response to the goal option of precision targeting being selected.

18. The method of claim 10, wherein:

presenting the plurality of goal options using the user interface comprises presenting the plurality of goal options including at least a goal option of providing resynchronizing therapy; and selecting using the processor one or more programmability options associated with the selected one or more goals comprises selecting the one or more programmability options including at least one of a programmability option of microburst and cycling or a programmability option of pulse-by-pulse patterning in response to the goal option of providing desynchronizing therapy being selected.

19. The method of claim 10, wherein the plurality of goal options comprises at least one of multi-symptom control, power efficiency, prevention of habituation, providing desynchronizing therapy, plasticity induction, precision targeting, or providing resynchronizing therapy, and the plurality of programmability options comprises wide parameter range, various stimulation frequency combinations, active recharge options, microburst and cycling, program scheduling, and pulse-by-pulse patterning.

20. A non-transitory computer-readable storage medium including instructions, which when executed by a system, cause the system to perform a method for delivering neurostimulation from a stimulation device, the method comprising:

receiving one or more goal options selected from a plurality of goal options each including at least one goal for deep brain stimulation (DBS);

selecting one or more programmability options associated with the received one or more goal options a plurality of programmability options based on a predetermined relationship mapping each goal option of the plurality of goal options to one or more programmability options of the plurality of programmability options, the programmability options each allowing one or more aspects of at least one of a pattern of neurostimulation pulses or the delivery of the neurostimulation according to the pattern of neurostimulation pulses to be programmable;

receiving programming information required by the selected one or more programmability options;

determining a pattern of neurostimulation pulses for the selected one or more goal options using the received programming information; and generating information for programming the stimulation device to deliver the neurostimulation according to the determined pattern of neurostimulation pulses.

* * * * *